(12) United States Patent
Thomson

(10) Patent No.: US 10,724,995 B2
(45) Date of Patent: Jul. 28, 2020

(54) VISCOSITY ESTIMATION FROM DEMODULATED ACOUSTIC EMISSION

(71) Applicant: AKTIEBOLAGET SKF, Göteborg (SE)

(72) Inventor: Allan Thomson, Lanark (GB)

(73) Assignee: AKTIEBOLAGET SKF, Gothenburg (SE)

(*) Notice: Subject to any disclaimer, the term of this patent is extended or adjusted under 35 U.S.C. 154(b) by 551 days.

(21) Appl. No.: 15/104,350

(22) PCT Filed: Dec. 15, 2014

(86) PCT No.: PCT/EP2014/077826
§ 371 (c)(1),
(2) Date: Jun. 14, 2016

(87) PCT Pub. No.: WO2015/091394
PCT Pub. Date: Jun. 25, 2015

(65) Prior Publication Data
US 2016/0313228 A1   Oct. 27, 2016

(30) Foreign Application Priority Data

Dec. 17, 2013   (GB) .................................. 1322268.2

(51) Int. Cl.
*G01N 29/14* (2006.01)
*G01M 13/045* (2019.01)
(Continued)

(52) U.S. Cl.
CPC .......... *G01N 29/14* (2013.01); *G01M 13/045* (2013.01); *G01N 29/4418* (2013.01); *G01N 33/2888* (2013.01); *G01N 33/30* (2013.01)

(58) Field of Classification Search
CPC .... G01N 29/14; G01N 33/30; G01N 33/2888; G01N 29/4418; G01N 2011/0073; G01M 13/045; F16C 33/66
(Continued)

(56) References Cited

U.S. PATENT DOCUMENTS 5,602,761 A * 2/1997 Spoerre .................. G01H 1/003
                                                    702/179
6,339,961 B1   1/2002 Goodman et al.
(Continued)

FOREIGN PATENT DOCUMENTS

CN         1580533 A     2/2005
CN         1659427 A     8/2005
(Continued)

OTHER PUBLICATIONS

Merriam Webster Dictionary Online term Multivariate. Accessed Oct. 23, 2018. pp. 1-2. https://www.merriam-webster.com/dictionary/multivariate. (Year: 2018).*
(Continued)

*Primary Examiner* — Kamini S Shah
*Assistant Examiner* — John E Johansen
(74) *Attorney, Agent, or Firm* — Garcia-Zamor Intellectual Property Law, LLC; Ruy Garcia-Zamor; Bryan Peckjian

(57) ABSTRACT

A process for estimating the lubricant viscosity in a bearing comprises the steps of: monitoring acoustic emissions from the bearing with an acoustic emission sensor; monitoring the bearing for at least one of speed, load and temperature; demodulating the acoustic emission signal from the acoustic emission sensor; calculating the root mean square values of the demodulated acoustic emission signal and storing the calculated root mean square values; aligning the root mean square values with values of one or more of speed, load and
(Continued)

temperature and storing the aligned values; using the aligned root mean square values, and at least one of speed, load and temperature in a model which calculates viscosity and/or viscosity ratio from the aligned values.

13 Claims, 6 Drawing Sheets

(51) Int. Cl.
*G01N 29/44* (2006.01)
*G01N 33/28* (2006.01)
*G01N 33/30* (2006.01)

(58) Field of Classification Search
USPC ........................................ 703/22, 2
See application file for complete search history.

(56) References Cited

U.S. PATENT DOCUMENTS

| | | | |
|---|---|---|---|
| 7,813,906 B2* | 10/2010 | Shiromaru | G01M 13/045 703/6 |
| 2005/0246150 A1 | 11/2005 | Shiromaru et al. | |
| 2008/0065354 A1 | 3/2008 | Yoshioka et al. | |
| 2011/0265569 A1* | 11/2011 | Ganji | F16C 19/52 73/587 |
| 2013/0326301 A1* | 12/2013 | May | G01V 3/38 714/746 |

FOREIGN PATENT DOCUMENTS

| | | |
|---|---|---|
| CN | 101846656 A | 9/2010 |
| CN | 101846656 B | 11/2011 |
| CN | 103394972 A | 11/2013 |
| CN | 101458158 A | 6/2016 |
| EP | 1598569 A1 | 11/2005 |
| GB | 2430034 A | 3/2007 |
| WO | 2010085971 A1 | 8/2010 |

OTHER PUBLICATIONS

Merriam Webster Dictionary Online term Regression. Accessed Oct. 23, 2018. pp. 1-5. https://www.merriam-webster.com/dictionary/regression. (Year: 2018).*
SKF Application Note Analysis and Interpretation of SKF Acoustic Emission Enveloping (AEE) Measurements p. 1 Paragraph 1 to p. 3 the Last Paragraph, p. 12 the Last Paragraph, p. 15 the Last Paragraph of the Description and Figs. 1, 3-4, 20 (Jan. 8, 2013).
SKF: 1 Analysis and interpretation of SKF Acoustic Emission Enveloping (AEE) measurements 11, SKF Application Note CM3155/1 EN, Aug. 1, 2013 (Aug. 1, 2013), pp. 1-20, XP055110811, Retrieved from the Internet: URL:http://www.skf.com/binary/tcm:12-76939 /CM3155 EN Analysis of AEE Measurements.pdf.
K.M. Sathiah Kumar et al: "Estimation of AE parameters for monitoring bearing in a lathe using multiple regression and GMDH" In: "Proceedings of the 2008 ASME International Mechanical Engineerign Congress and Exposition", Nov. 6, 2008 (Nov. 6, 2008), ASME, XP00817001.

* cited by examiner

Examples of Model Parameters

| Date | Time | RMS of demodulated acoustic emission signal | RPM | Temp (C) | Visc (mm²/sec) | V1 (mm²/sec) | kappa | Load (kN) |
|---|---|---|---|---|---|---|---|---|
| 20110207 | 13:50:46 | 17.44978 | 80 | 44 | 176.1568 | 41.48132 | 4.246653 | 275 |
| 20110207 | 14:05:27 | 17.39521 | 80 | 44 | 176.1568 | 41.48132 | 4.246653 | 275 |
| 20110207 | 14:18:17 | 17.62747 | 80 | 44 | 176.1568 | 41.48132 | 4.246653 | 275 |
| 20110207 | 14:31:25 | 17.04755 | 80 | 44 | 176.1568 | 41.48132 | 4.246653 | 275 |
| 20110207 | 14:43:43 | 16.51371 | 80 | 45 | 168.7765 | 41.48132 | 4.068735 | 275 |
| 20110207 | 14:56:38 | 17.28032 | 80 | 45 | 168.7765 | 41.48132 | 4.068735 | 275 |
| 20110207 | 15:09:57 | 17.29751 | 80 | 45 | 168.7765 | 41.48132 | 4.068735 | 275 |
| 20110207 | 15:23:00 | 17.57015 | 80 | 45 | 168.7765 | 41.48132 | 4.068735 | 275 |
| 20110207 | 15:36:14 | 17.61097 | 80 | 46 | 161.7262 | 41.48132 | 3.898771 | 275 |
| 20110207 | 19:08:20 | 21.28801 | 80 | 47 | 154.9879 | 41.48132 | 3.736329 | 275 |
| 20110209 | 02:22:09 | 51.65215 | 80 | 67 | 66.62998 | 41.48132 | 1.606265 | 550 |
| 20110209 | 02:43:41 | 48.84537 | 80 | 65 | 72.51652 | 41.48132 | 1.748173 | 550 |
| 20110209 | 03:02:56 | 45.08585 | 80 | 64 | 75.64791 | 41.48132 | 1.823662 | 550 |
| 20110209 | 03:22:33 | 41.72413 | 80 | 62 | 82.31364 | 41.48132 | 1.984354 | 550 |
| 20110209 | 03:42:03 | 38.71427 | 80 | 61 | 85.85959 | 41.48132 | 2.069838 | 550 |
| 20110209 | 04:00:36 | 37.15665 | 80 | 60 | 89.55591 | 41.48132 | 2.158945 | 550 |
| 20110209 | 04:18:55 | 34.75286 | 80 | 59 | 93.40926 | 41.48132 | 2.251839 | 550 |
| 20110209 | 12:58:55 | 22.04976 | 80 | 54 | 115.2954 | 41.48132 | 2.779453 | 550 |
| 20110209 | 13:13:11 | 21.53981 | 80 | 54 | 115.2954 | 41.48132 | 2.779453 | 550 |
| 20110209 | 13:26:51 | 20.90484 | 80 | 54 | 115.2954 | 41.48132 | 2.779453 | 550 |
| 20110209 | 13:40:13 | 21.78934 | 80 | 54 | 115.2954 | 41.48132 | 2.779453 | 550 |
| 20110210 | 09:16:37 | 54.43011 | 81 | 67 | 66.62998 | 41.01785 | 1.624414 | 1100 |
| 20110210 | 09:35:03 | 52.39746 | 81 | 66 | 69.51223 | 41.01785 | 1.694683 | 1100 |
| 20110210 | 09:54:42 | 51.87693 | 81 | 65 | 72.51652 | 41.01785 | 1.767926 | 1100 |
| 20110210 | 10:13:49 | 49.84043 | 81 | 64 | 75.64791 | 41.01785 | 1.844268 | 1100 |
| 20110210 | 10:31:44 | 48.91358 | 81 | 63 | 78.91173 | 41.01785 | 1.923839 | 1100 |
| 20110210 | 19:06:54 | 40.43741 | 81 | 60 | 89.55591 | 41.01785 | 2.18334 | 1100 |
| 20110210 | 19:19:17 | 40.18514 | 81 | 60 | 89.55591 | 41.01785 | 2.18334 | 1100 |
| 20110210 | 19:31:36 | 40.06541 | 81 | 60 | 89.55591 | 41.01785 | 2.18334 | 1100 |
| 20110210 | 19:43:52 | 40.49914 | 81 | 60 | 89.55591 | 41.01785 | 2.18334 | 1100 |

FIG. 4

Multivariate regression fit of kappa as a function of RMS of a demodulated acoustic emission signal and load utilizing the equation $y = a + b/x_1 + c/x_2$

VISCOSITY ESTIMATION FROM DEMODULATED ACOUSTIC EMISSION

CROSS-REFERENCE TO RELATED APPLICATIONS

This application is the U.S. National Stage of International Application No. PCT/EP2014/077826 filed on Dec. 15, 2014, which claims the benefit of priority from GB Patent Application No. 1322268.2 filed on Dec. 17, 2013, the contents of which are both herein incorporated by reference in their entirety.

FIELD OF THE INVENTION

The present invention relates to a method for monitoring the lubrication condition in a lubricated rolling element bearing by analyzing a demodulated acoustic emission signal, and in particular to estimating the viscosity of the lubrication film in the bearing.

BACKGROUND OF THE INVENTION

In order for a rolling element bearing to operate in a reliable way it must be lubricated adequately. Lubricant prevents metal to metal contact within the bearing and protects surfaces within the bearing against corrosion. It is therefore important to select the proper lubricant and lubrication method for each individual bearing application, as well as a correct maintenance program.

In some instances, particularly concerning large machinery that is not easily accessible, such as wind turbines, it is desirable to provide a method of monitoring the lubrication condition of a bearing without affecting normal running of the bearing.

A method of monitoring the lubrication condition of a rolling element bearing by means of determining a lubrication parameter indicative of the lubrication condition is described in WO2010/085971.

In a first step, high-frequency structure-borne acoustic emissions are measured. The measured acoustic emissions are generated as a result of asperity contact between rolling surfaces of the bearing, and provide a measured signal. In a second step, emitted acoustic energy is extracted from the measured signal. In a third step, the lubrication parameter is determined from the emitted acoustic energy, on the basis of a power-law relationship between acoustic energy and the lubrication parameter. The lubrication parameter used to indicate lubrication condition is either specific lubrication film thickness (Lambda) or lubricant viscosity ratio (Kappa). The value of Kappa is the ratio of a lubricant's actual viscosity to a minimum required viscosity that the lubricant must possess in order to form an adequate lubricant film. The required viscosity is dependent on the size and speed of rotation of the bearing whilst actual viscosity is dependent on the lubricant and temperature.

In bearing life calculations the actual viscosity in the viscosity ratio (Kappa) is presumed from the viscosity grade of the lubricant, the lubricant operating temperature and bearing speed.

A bearing life model is a statistical model which says that under a certain set of operating parameters a certain percentage (for example 90%) of bearings of the same type and lubricated in the same way will last a certain number of hours before failure. ISO 281:2007 entitled, "Rolling Bearings—Dynamic Load Ratings and Life" describes such a model. There are two problems with this type of model. The first is that the model cannot predict which particular bearings will be the bearings that last the predicted number of hours and which will fail prior to the predicted life. The second is that the presumed actual viscosity used in the viscosity ratio may not be representative of the actual viscosity if the viscosity were measured.

If rather than presuming the actual viscosity it can be monitored, then rather than basing a bearing life calculation on a presumption, the bearing life calculation can be based on a monitored estimated actual viscosity ratio in the bearing concerned. This would be of particular value where bearings are of high value and are difficult to access, as servicing or repair of the bearing can be scheduled prior to failure.

Whilst WO2010/085971 attempts to provide a solution to the above-mentioned problem, it may be difficult to identify acoustic emission signals associated with asperity contacts occurring as the viscosity ratio falls only marginally below 0.5.

Also, monitoring a raw acoustic emission signal requires sampling and processing equipment capable of sampling and processing MHz signals. Such equipment is sophisticated, expensive and generally for use in the laboratory rather than in the field.

It would therefore be desirable to be able to ascertain lubricant viscosity, and hence lubricant viscosity ratio more accurately.

It would also be desirable to be able to ascertain lubricant viscosity and lubricant viscosity ratio using less sophisticated equipment.

SUMMARY OF THE INVENTION

According to the invention there is provided a process for estimating the lubricant viscosity in a lubricated bearing comprising the steps of:
i) monitoring acoustic emissions from the bearing with an acoustic emission sensor during an acquisition period and time stamping the acquisition period;
ii) monitoring the bearing for at least one of speed, load and temperature and storing in a database time stamped monitored values of the at least one of speed, load and temperature;
iii) demodulating the acoustic emission signal from the acoustic emission sensor;
iv) calculating the root mean square values of the demodulated acoustic emission signal in a data processor and storing the calculated root mean square values in the database;
v) aligning in time the values of the root mean square of the demodulated acoustic emission signal with values of one or more of speed, load and temperature and storing the aligned values in the database;
vi) using the aligned values of the root mean square of the demodulated acoustic emission signal, and at least one of speed, load and temperature in a model which calculates viscosity and/or viscosity ratio from the aligned values.

According to a second aspect of the invention there is provided a process for creating a mathematical model of viscosity or viscosity ratio comprising the steps of:
i) running a bearing with new lubricant at different speeds, loads or temperatures;
ii) monitoring acoustic emissions from the bearing with an acoustic emission sensor during an acquisition period and time stamping the acquisition period;

iii) monitoring the bearing for at least one of speed, load and temperature and storing in a database time stamped monitored values of the at least one of speed, load and temperature;
iv) demodulating the acoustic emission signal from the acoustic emission sensor;
v) calculating the root mean square values of the demodulated acoustic emission signal in a data processor and storing the calculated root mean square values in the database;
vi) aligning in time the values of the root mean square of the demodulated acoustic emission signal with values of one or more of speed, load and temperature and storing the aligned values in the database;
vii) calculating the viscosity of the new lubricant from a known viscosity/temperature data;
viii) storing the aligned values of the root mean square of the demodulated acoustic emission signal, and at least one of speed, load, temperature and calculated viscosity in a database;
ix) performing multi-variate regression analysis on the stored values and developing a "best fit" model where viscosity or Kappa is the dependent variable and the root means square of the demodulated acoustic emission signal and one of speed, load and temperature are independent variables.

Preferably, the values of the root mean square of the demodulated acoustic emission signal are calculated over an acquisition period, and preferably the acquisition period is aligned in time with values of at least one of speed, load and temperature.

The acquisition period is preferably between 0.5 and 30 seconds, depending on the rotational speed of the monitored bearing. Smaller acquisition periods are used with faster running bearings and longer acquisition periods with slower running bearings. For example, an acquisition period of less than 1 second, for example 0.8 seconds, may be used with a bearing rotating at 3600 rpm or greater, whereas an acquisition period of 30 seconds may be used with a bearing rotating at 5 rpm.

Ideally, the acquisition period is sufficiently long to capture four rotations of the bearing.

Advantageously, the model of step vi in the first aspect of the invention is a model created according to the process of the second aspect of the invention.

The process for estimating the lubricant viscosity in a bearing may include the step of establishing whether the model has already been created and if not creating the model according to the process of the second aspect of the invention.

The process for estimating the lubricant viscosity in a bearing may comprise the further step of using the calculated value of viscosity or Kappa in a bearing life model.

BRIEF DESCRIPTION OF THE DRAWINGS

In the drawings, which are by way of example:
FIG. 4 is a table showing collected model parameters.

DETAILED DESCRIPTION OF THE PREFERRED EMBODIMENTS

Figure 1A:
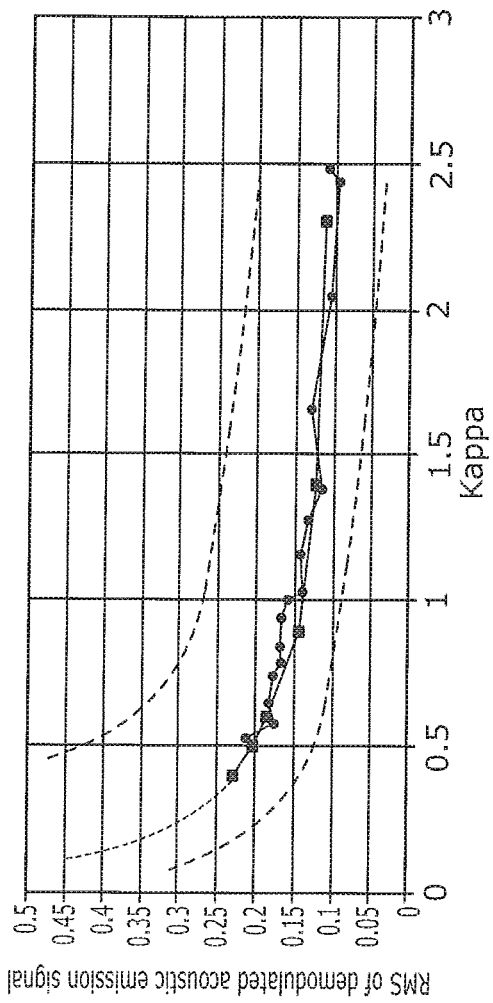
FIG. 1A shows a graph illustrating for an oil lubricant the variation of lubricant viscosity ratio Kappa with the root means square of the demodulated acoustic emission signal.
Figure 1B:
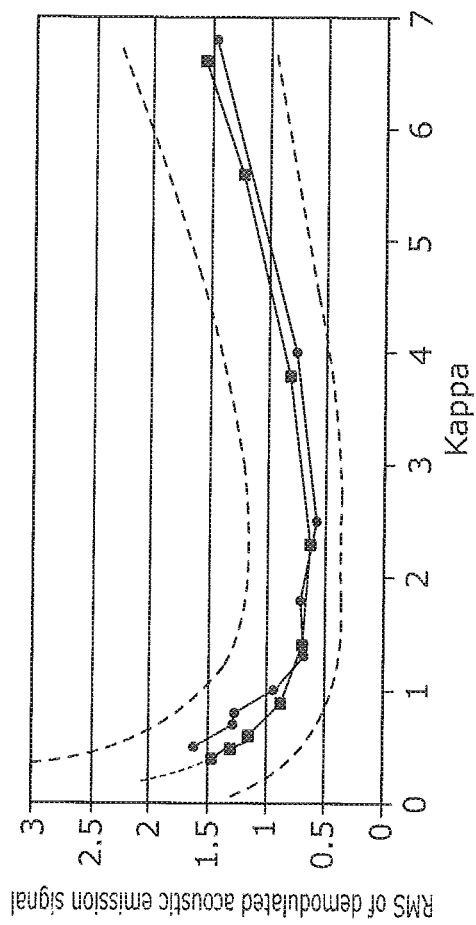
FIG. 1B shows a graph illustrating for a grease lubricant the variation of lubricant viscosity ratio Kappa with the root means square of the demodulated acoustic emission signal.

FIGS. 1A and 1B show graphs for oil and grease respectively of the typical variation in root means square (RMS) of demodulated acoustic emission signal with changing lubricant viscosity Kappa. The graphs were established by experiment and form part of the state of the art.

As can be seen, for oil the RMS of the demodulated acoustic emission signal increases significantly when Kappa falls below 1.5, and for grease when Kappa falls below 1.0.

The symbol "●" represents the measured changes in the RMS of the demodulated acoustic emission signal with changing Kappa. For each graph the theoretical curve of variation of the RMS of the demodulated acoustic emission signal where the bearing is rotating at a notional speed is denoted by the symbol "■". The theoretical curve is the curve that is the "best fit" to the measured data represented by the symbol "●".

In each graph, two plots in broken line form are shown, one above and one below the plots of theoretical and measured variation of the RMS of the demodulated acoustic emission signal with Kappa. In each graph the upper and lower plots in broken line form represent the variation in of the RMS of the demodulated acoustic emission signal with kappa for a bearing rotating more quickly and more slowly respectively than the notional speed.

The prior art, measuring raw acoustic emission signals shows the detection of asperity contacts, which occur when Kappa falls to 0.5. By looking at the RMS of the demodulated acoustic emission signal, changes in Kappa well above 0.5 can be detected and hence a greater knowledge of the changing condition of the bearing can be obtained.

Figure 2:
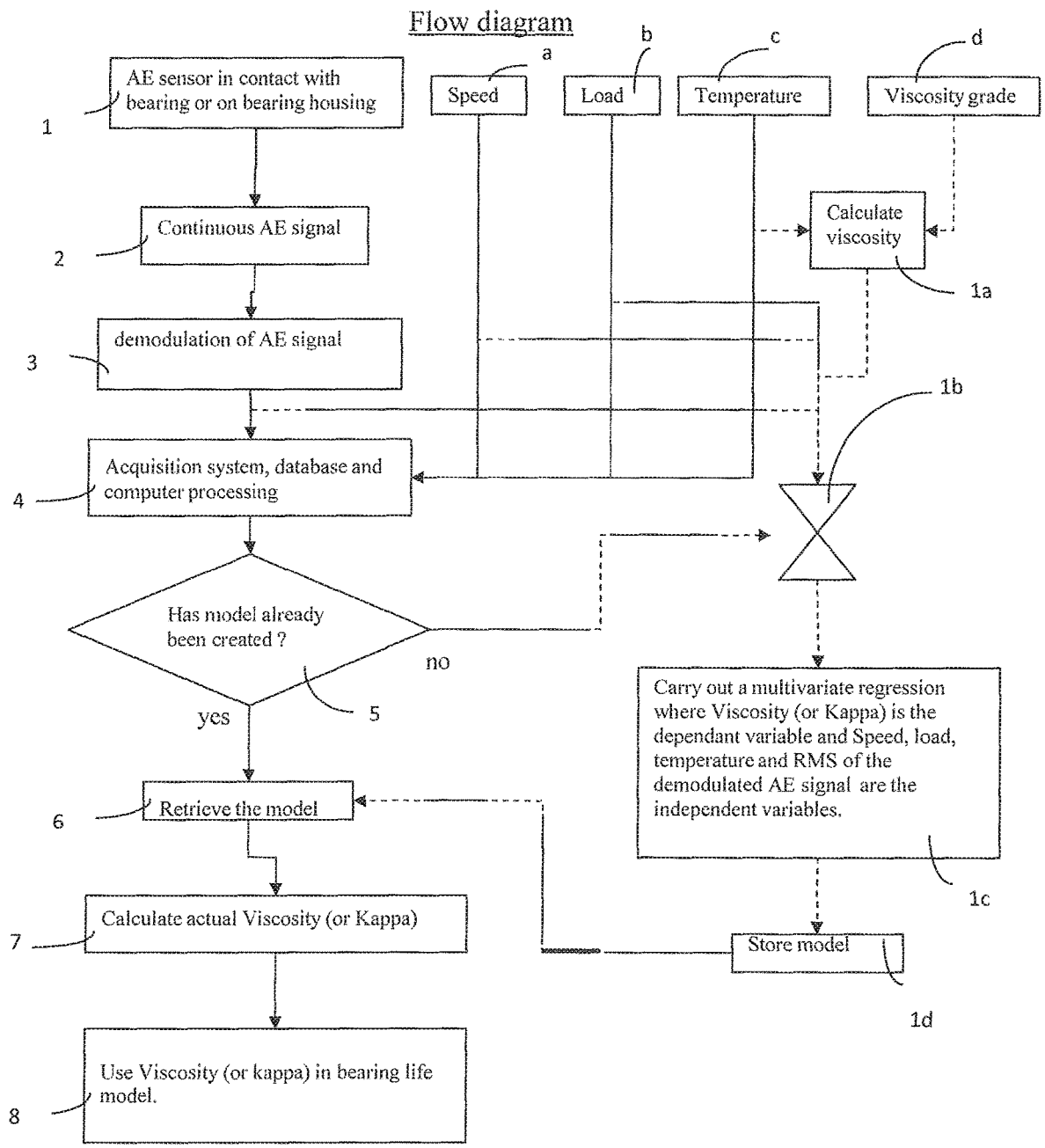
FIG. 2 is a flow diagram illustrating the process of the invention.

The flow diagram shown in FIG. 2 illustrates the process of the invention.

In step 1, an acoustic emission sensor (referred to as an AE sensor in FIG. 2) is placed in contact with a bearing or bearing housing and described in greater detail with reference to FIG. 6.

In step 2 the acoustic emission sensor generates a continuous acoustic emission signal from the bearing. The system acquiring the acoustic emission signal for subsequent demodulation will typically have a sampling rate of around 1 to 10 ksps (kilo samples per second) depending on the limitations of the acquisition system and the speed of rotation of the shaft supported by the monitored bearing. Higher shaft speeds allow for faster sampling rates with better RMS variations, but lower shaft speeds often result in lower sampling rates. This is because it is desirable that data is captured over a number of revolutions of the bearing. Looking at two bearings rotating at different speeds, the time period required for the bearing that is rotating more slowly will be greater than the time period required for the more quickly rotating bearing to rotate the same number of times. The system for acquiring the acoustic emission signal typically has a capacity for a maximum number of samples in any one acquisition. In the case of a bearing rotating slowly the combination of the time required for the desired number of revolutions of the bearing to be completed multiplied by a desired sampling rate may result in a total number of samples exceeding the capacity of the acquisition system, and hence it would be necessary to reduce the sampling rate of the system for acquiring the acoustic emission signal.

Figure 3:
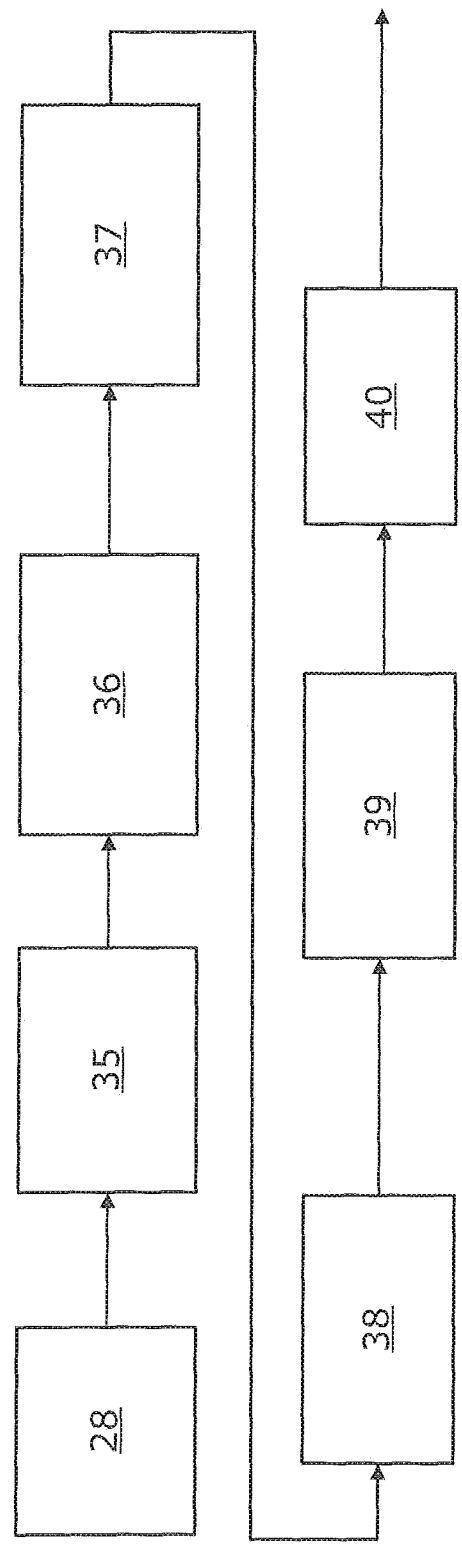
FIG. 3 is a block diagram of a signal processing system used in the invention.

In step 3 the raw acoustic emission signal is demodulated using a signal processing system as shown in FIG. 3.

In the processing system shown in FIG. 3 the output of an acoustic emission sensor 28 forms the input to a pre-amplifier 35 provides a required voltage gain. The amplified signal is passed through a high pass filter 36 set to 100 kHz, that is signals having frequency greater than 100 kHz pass through the filter and those having a lower frequency do not. The output of the high pass filter 36 forms the input to a low pass filter 37 set to 500 kHz, that is signals having frequency lower than 500 kHz pass through the filter and those having a higher frequency do not. The output of the low pass filter 37 forms the input to a full wave rectifier 38, the output of which forms the input to an anti-aliasing filter 39, the function of which is to remove noise introduced to the signal by passing the signal from the acoustic emission sensor 28 through the other components signal processing system. The anti-aliasing filter 39 outputs to a balanced driver 40, which conditions the signal to have power and impedance characteristics that provide for transmission thereof to the data acquisition system of step 4 of the process of the invention.

In addition to the acoustic emission sensor, the bearing or bearing housing is also equipped with other condition monitoring sensors, in this case a speed sensor a for monitoring the rotational speed of the bearing, a load sensor b for monitoring the load on the bearing and temperature sensor c for monitoring the bearing temperature. Instead of providing a single temperature sensor c, multiple temperature sensors may be provided, allowing the temperature of the bearing to be measured at different positions on the bearing.

The performance of step 4 requires a processor and data storage. The acquisition system therefore includes a processor and a database.

The outputs of the speed, load and temperature sensors form inputs to the processor of step 4 and are utilized in the processing step 4.

The demodulated acoustic emission signal from step 3 also forms an input to step 4.

All the inputs to step 4 are recorded in the database.

In step 4 the root mean square (RMS) of the demodulated acoustic emission signal is calculated, typically over an acquisition time of between 0.5 and 30 seconds, depending on the rotational speed of the bearing. Ideally, the acquisition period is sufficiently long to capture four rotations of the bearing.

The RMS of the demodulated acoustic emission signal represents the fluctuation in energy of the demodulated acoustic emission signal. However, the RMS of the demodulated acoustic emission signal has also proved to be proportional to the energy of a continuous raw acoustic emission signal as its fluctuations increase proportionally with its energy within the demodulation's filter band.

In a further processing step, the calculated values of the RMS of the demodulated acoustic emission signal are aligned with the speed, load and temperature signals. That is, the time stamping of the speed, load and temperature signals is aligned with the time stamping of the acquisition period, the acquisition period being the period for acquiring the acoustic emission signal for subsequent demodulation. In this way changes in the RMS of the demodulated acoustic emission can be correlated with variations in the other monitored parameters.

The process uses a model for the particular application of the monitored bearing. The model is created by operating the bearing and monitoring under controlled conditions with new lubricant. This allows a database of values of the RMS of the acoustic emission signal under different loads, speeds and temperatures to be built up when the actual viscosity is known, because the lubricant is new and can safely be assumed to have the viscosity indicated by the lubricant manufacturer.

In step 5 the process asks whether viscosity estimation model has already been created or not.

If the viscosity estimation model has not been created, the estimation routine is run. The speed a, load b, temperature c, demodulated acoustic emission signal from step 3, the RMS of the demodulated acoustic emission signal from step 4 are measured and the viscosity is calculated in step 1a for each measured temperature using the viscosity grade/temperature chart from the lubricant manufacturer.

In step 1b the parameters described above are collected.

Table 1 in FIG. 4 presents an example set of collected model parameters. In Table 1, the RMS of the demodulated acoustic emission signal is of an AC coupled circuit, temperature is measured in Celsius, Visc represents actual viscosity and V1 required viscosity, both in $mm^2$/second and load is measured in kN.

The time in hours, minutes and seconds is the time stamp for the parameters in a respective row, the acquisition period in this example for each sample being 3.2 seconds, to capture four rotations of the bearing rotating at 80 rpm.

The acquisition period used in creating the model is then used in the model when the process is used to monitor the same type of bearing in the field.

As can be seen for the table, the variable in the example is load, with nine or ten samples being taken for each load of 275 kN, 550 kN and 1100 kN. The nominal speed is essentially unchanged, being 80 or 81 rpm for all loads.

A database of values of the RMS of demodulated acoustic emission signal is built up by testing under different loads, speeds and temperatures.

In step 1c a multivariate regression analysis is performed where viscosity (Kappa) is the dependent variable and speed, load and temperature and RMS of demodulated acoustic emission are the independent variables.

The outputs are the equation and its constants, which together represent the model.

The model is stored in step 1d for future in field use.

Figure 5:
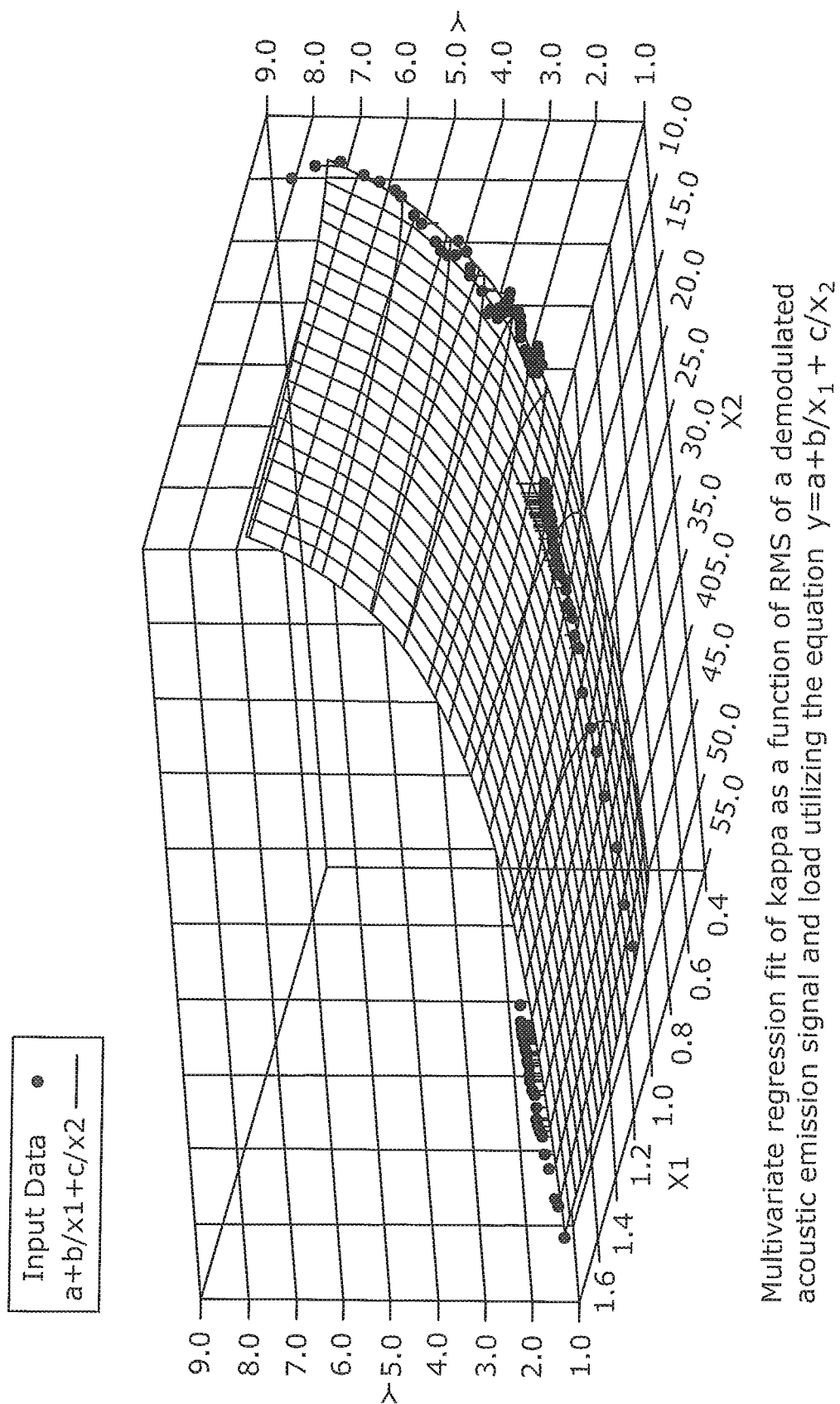
FIG. 5 is a three axis graph representing an example of a model used in the process of the invention.

FIG. 5 is a three axis graph illustrating the multivariate regression analysis. In this case the "best fit" equation, the model, describing the three axis curve is $y=a+b/x1+c/x2$, where x1 is the ratio of measured load to nominal load, x2 is the RMS of demodulated acoustic emission signal and a, b and c are constants.

With the model the RMS of demodulated acoustic emission signal may be measured and the equation of the model solved for viscosity or the viscosity ratio (Kappa), which is done in step 7.

In step 8 the calculated actual viscosity or viscosity ratio (Kappa) value is then used in the bearing life model. The bearing life model used is based on the ISO 281, "Rolling Bearings—dynamic load ratings and rating life".

In the flow diagram of FIG. 2, the dashed flow lines represent paths and actions only utilized during the initial creation of the viscosity or Kappa model.

The process of the invention provides an estimated actual value of viscosity and/or viscosity ratio (Kappa) based on monitoring the condition of a bearing in use in a piece of equipment, instead of the actual lubricant viscosity or Kappa value when the lubricant was new. The initial Kappa value may be 4 for example, but the estimated actual value may only be 1.5 indicating a much shorter bearing life. With this knowledge, action may be taken, for example the lubricant may be changed, or the bearing scheduled for replacement at an earlier time than would have been indicated using the Kappa value when the lubricant was new.

Figure 6:
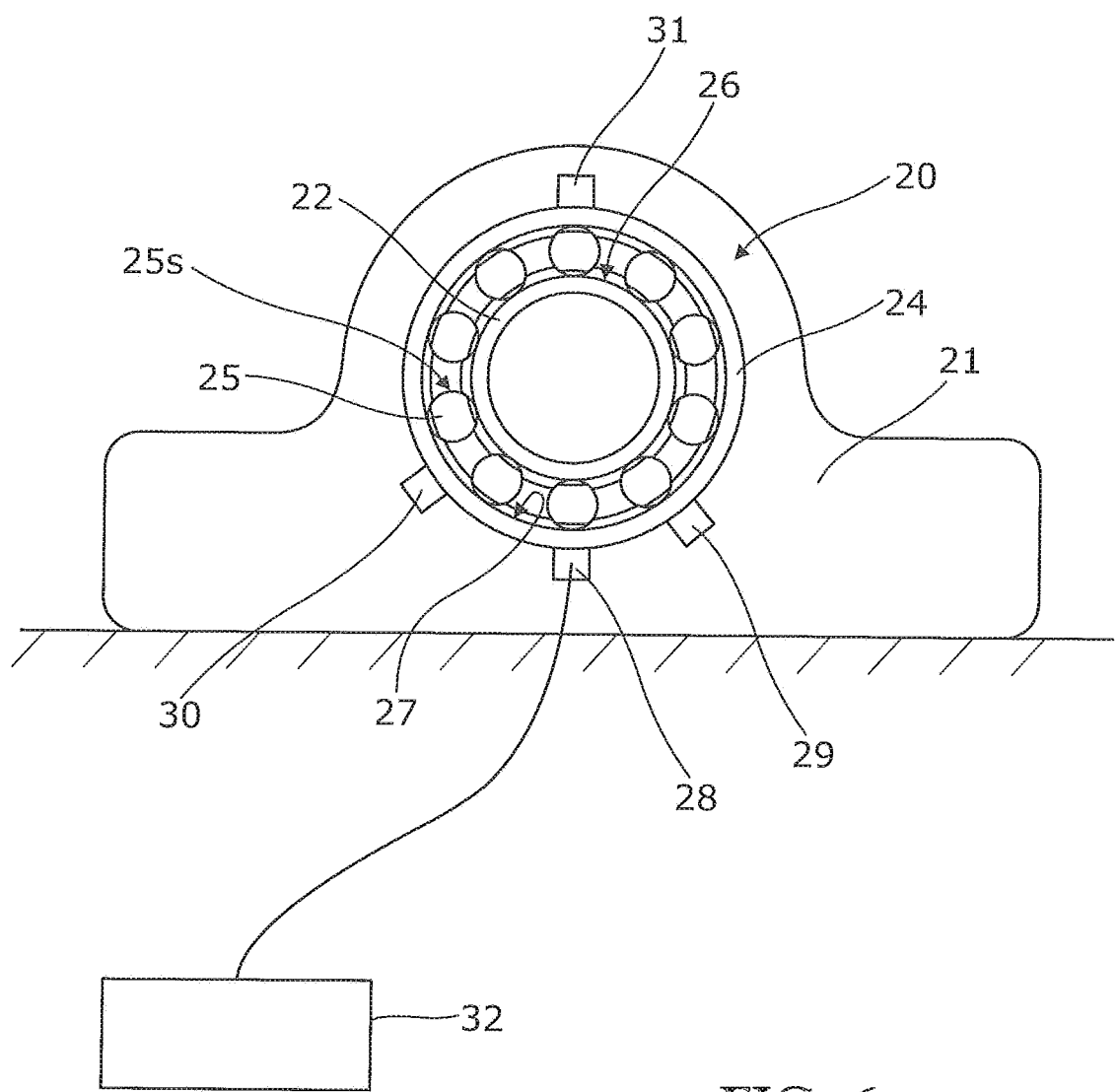
FIG. 6 is schematic representation of an instrumented bearing.

FIG. 6 shows an example of a system comprising a bearing to be monitored and a lubrication condition monitoring device that is arranged to execute the method according to the invention. The bearing in this example is a radial rolling element bearing 20, comprising an inner ring 22, an outer ring 24 and rolling elements 25 disposed therebetween. Thus an outer diameter of the bearing inner ring 22 defines an inner raceway 26 for the rolling elements 25 and an inner diameter of the bearing outer ring 24 defines an outer raceway 27. Further, the bearing 20 is mounted in a housing 21 and is lubricated with an oil (not shown).

The lubrication condition monitoring device comprises an acoustic emission sensor 28, a temperature sensor 29 recording temperature at a specific position on the bearing, a rotational speed sensor 30, a load sensor 31 and a signal processor 32 that is arranged to record and process the acoustic emission signal, temperature, rotational speed and load signals, detected by the sensor according to the process steps set out in FIG. 2. In the example of FIG. 1, the acoustic emission sensor 28 is mounted on the bearing outer ring 24, which ring is non-rotational during bearing operation. The acoustic emission sensor 28 can also be positioned on the housing 21, or on some other fixed structure to which the bearing is mounted. In applications where the bearing inner ring 22 is non-rotational in operation, the acoustic emission sensor 28 may be mounted, for example, in a notch in an inner diameter (bore) of the inner ring 22.

During bearing operation, an outer surface 25s of the rolling elements 25 is in rolling contact with the inner raceway 26 and the outer raceway 27. These rolling contact surfaces 25s, 26, 27 have a certain roughness due to asperities. Depending on the lubrication condition in the bearing and in particular the lubricant viscosity, the oil film separating the rolling contact surfaces may not be sufficiently thick to prevent asperity contact between the rolling element surfaces 25s and the bearing raceways 26, 27. Asperity contact starts to occur when Kappa falls below 0.5. This asperity contact (metal-to-metal contact) within the bearing 20 generates acoustic emission. The level of acoustic emission detected by an acoustic emission sensor mounted in direct or indirect contact with a bearing ring is therefore indicative of the degree of asperity contact between the rolling element surfaces and the bearing raceways, and is thus indicative of the lubrication condition within the bearing.

To ensure proper transmission of the propagated stress waves to the acoustic emission sensor 28, it is important that there is good mechanical contact between the acoustic emission sensor 28 and surface of the bearing or bearing housing to which the sensor 28 is mounted. This can be achieved in different ways. One way is to machine a flat surface in the outside diameter of the bearing outer ring 24 and mount the acoustic emission sensor on the flat surface. Since the acoustic emission sensor may be quite small, this mounting technique may also be used relatively small bearings. Another way of mounting the acoustic emission sensor to the bearing is to manufacture the acoustic emission sensor such that its detecting surface has the same radius of curvature as the bearing surface with which it will be in contact. This will also enable a mating contact between the acoustic emission sensor and the bearing. For larger bearings, it is also possible to machine a notch in the outer ring in which the acoustic emission sensor can be mounted. As will be understood, any machining in a bearing ring should be performed such that the function of the bearing is not impaired.

In addition to ensuring a mating fit between the contacting surfaces of the bearing or bearing housing and the acoustic emission sensor, the transmission of acoustic waves to the acoustic emission sensor can be improved by using grease, e.g. vacuum grease, or an oil as a coupling medium between the sensor and the surface to which it is mounted.

The acoustic emission sensor 28 can be mounted at any angular position of the bearing. The mounting position will depend on the available space in the machine in which the bearing is used. A preferred mounting position for the acoustic emission sensor is a position that is in line with the direction of the load on the bearing. Hence, for a radially loaded bearing, the acoustic emission sensor 28 should be radially mounted. In the case of thrust bearings, for example, which are subjected to axial loading, the acoustic emission sensor should be axially mounted, i.e. on a side face of the bearing ring that is non-rotational in operation. Furthermore, the mounting position is preferably in line with the bearing loaded zone and in line with the region of rolling contact. Since the acoustic waves propagate from the contact surface between the rolling elements 25s and the raceways 26, 27, the signal quality will be best directly opposite the contact region. This will reduce interfering acoustic waves caused by reflections from the measured signal and from acoustic waves from other sources in the machinery. It will also improve the signal-to-noise ratio of the signal.

Using the RMS of the demodulated acoustic emission signal allows less expensive data acquisition and processing equipment to be used. Also, the degree of expertise required to analyze the signal produced by the process of the invention is significantly less than that required to analyze raw acoustic emission data.

Also, analysis according to the process of the invention allows all values of lubricant viscosity to be measured not just viscosities indicating asperity contacts. The process of the invention may therefore provide information indicating that lubricant viscosity is trending towards 0.5. This information is valuable in terms of equipment operation and maintenance.

The invention claimed is:
1. A process for estimating the lubricant viscosity in a lubricated bearing, the process comprising steps of:
   i) monitoring acoustic emissions from the bearing using an acoustic emission sensor during an acquisition period and time stamping the acquisition period;
   ii) monitoring the lubricated bearing for a speed, a load, and a temperature and storing in a database time stamped monitored values of the speed, the load and the temperature;
   iii) demodulating the acoustic emission signal from the acoustic emission sensor;
   iv) calculating root mean square values of the demodulated acoustic emission signal using a data processor and storing the calculated root mean square values in the database;
   v) aligning in time the values of the root mean square of the demodulated acoustic emission signal with values of the speed, the load and the temperature and storing the aligned values in the database; and
   vi) using the aligned values of the root means square of the demodulated acoustic emission signal, and the speed, the load and the temperature in a model which calculates at least one of a viscosity and a viscosity ratio of the lubricant in the lubricated bearing from the aligned values, wherein the model:
  a) is processed by the data processor,
  b1) utilizes the speed, the load and the temperature,
  b2) utilizes a viscosity or a viscosity ratio of the new lubricant calculated from a known viscosity/temperature data;
  c) utilizes aligned values of the root mean square of the demodulated acoustic emission signal, the speed, the load and the temperature, and the calculated viscosity stored in the database; and
  d) a multi-variate regression analysis performed on the stored values and a "best fit" model developed where one of the viscosity or a Kappa is the dependent variable and the root mean square of the demodulated acoustic emission signal and the speed, the load and the temperature are independent variables, wherein the "best fit" model is defined by a "best fit" three-axis curve defined by $y = a + b/x_1 + c/x_2$, wherein $x_1$ is a ratio of a measured load to a nominal load, $x_2$ is the root mean square of the demodulated acoustic emission signal, and a, b, and c are constants.

2. A process according to claim 1, wherein the step of using the calculated value of the viscosity or the viscosity ratio in a bearing life model utilizes the calculated value of the viscosity.

3. A process according to claim 1, wherein the step of using the calculated value of the viscosity or the viscosity ratio in the bearing life model utilizes the calculated value of the viscosity ratio.

4. A process according to claim 1, wherein the root mean square values of the demodulated acoustic emission signal are calculated over an acquisition time of between zero point five (0.5) and thirty (30) seconds, and wherein the acquisition period is long enough to capture a minimum of four (4) rotations of the lubricated bearing.

5. The process of claim 1, wherein the step of demodulating the acoustic emission signal from the acoustic emission sensor (step iv) further comprises the following steps:
  a) passing an output of the acoustic emission sensor through a pre-amplifier to generate an amplified signal;
  b) passing the amplified signal through a high pass filter and a low pass filter to generate a filtered signal; and
  c) passing the filtered signal through a full wave rectifier, an anti-aliasing filter, and a balanced driver to generate the demodulated acoustic emission signal.

6. A process according to claim 5, wherein the step of using the calculated value of the viscosity or the viscosity ratio in the bearing life model utilizes the calculated value of the viscosity.

7. A process according to claim 5, wherein the step of using the calculated value of the viscosity or the viscosity ratio in the bearing life model utilizes the calculated value of the viscosity ratio.

8. A process according to claim 5, wherein the root mean square values of the demodulated acoustic emission signal are calculated over an acquisition time of between zero point five (0.5) and thirty (30) seconds, and wherein the acquisition period is long enough to capture a minimum of four (4) rotations of the lubricated bearing.

9. The process according to claim 1, wherein the model of step vi is created by:
  i) running a bearing with new lubricant at one of different speeds, different loads or different temperatures;
  ii) monitoring acoustic emissions from the bearing with the acoustic emission sensor during the acquisition period and time stamping the acquisition period;
  iii) monitoring the bearing for the speed, the load and the temperature and storing in the database time stamped monitored values of the speed, the load and the temperature;
  iv) demodulating the acoustic emission signal from the acoustic emission sensor;
  v) calculating the root mean square values of the demodulated acoustic emission signal using the data processor and storing the calculated root mean square values in the database;
  vi) aligning in time the values of the root mean square of the demodulated acoustic emission signal with values of the speed, the load and the temperature and storing the aligned values in the database;
  vii) calculating the viscosity of the new lubricant from a known viscosity/temperature data;
  viii) storing the aligned values of the root mean square of the demodulated acoustic emission signal, and the speed, the load and the temperature and calculated viscosity in the database;
  ix) performing multi-variate regression analysis on the stored values and developing a "best fit" model where one of the viscosity or the viscosity ratio is the dependent variable and the root mean square of the demodulated acoustic emission signal and the speed, the load and the temperature are independent variables.

10. A process for estimating the lubricant viscosity in a lubricated bearing, the process comprising steps of:
  i) determining whether a model has been created, wherein the model calculates at least one of a viscosity and a viscosity ratio from the aligned values, wherein the model is processed by the data processor and utilizes a speed, a load, and a temperature;
  ii) in a condition where the model has not been created, create the model in accordance with the following steps:
    a) running the lubricated bearing with new lubricant at one of different speeds, different loads, or different temperatures;
    b) monitoring acoustic emissions from the bearing with an acoustic emission sensor during an acquisition period and time stamping the acquisition period;
    c) monitoring the bearing for the speed, the load and the temperature and storing time stamped monitored values of the speed, the load and the temperature in a database;
    d) demodulating the acoustic emission signal from the acoustic emission sensor;
    e) calculating the root mean square values of the demodulated acoustic emission signal using a data processor and storing the calculated root mean square values in the database;
    f) aligning in time the values of the root mean square of the demodulated acoustic emission signal with values of the speed, the load and the temperature and storing the aligned values in the database;
    g) calculating the viscosity of the new lubricant from a known viscosity/temperature data;
    h) storing the aligned values of the root mean square of the demodulated acoustic emission signal, and the speed, the load and the temperature, and calculated viscosity in a database; and
    i) performing multi-variate regression analysis on the stored values and developing a "best fit" model where one of the viscosity or the viscosity ratio is the dependent variable and the root mean square of the demodulated acoustic emission signal and the at least one of the speed, the load and the temperature are independent variables, wherein the "best fit" model is defined by a "best fit" three-axis curve defined by $y=a+b/x_1+c/x_2$, wherein $x_1$ is a ratio of a measured load to a nominal load, $x_2$ is the root mean square of the demodulated acoustic emission signal, and a, b, and c are constants; and iii) determining one of the viscosity or the viscosity ratio of the lubricant in the lubricated bearing in accordance with the following steps:
  A) monitoring acoustic emissions from the bearing using an acoustic emission sensor during an acquisition period and time stamping the acquisition period;
  B) monitoring the lubricated bearing for the speed, the load and the temperature and storing in a database time stamped monitored values of the speed, the load and the temperature;
  C) demodulating the acoustic emission signal from the acoustic emission sensor in accordance with the following steps:
    a) passing an output of the acoustic emission sensor through a pre-amplifier to generate an amplified signal;
    b) passing the amplified signal through a high pass filter and a low pass filter to generate a filtered signal;
    c) passing the filtered signal through a full wave rectifier, an anti-aliasing filter, and a balanced driver to generate the demodulated acoustic emission signal;
  D) calculating root mean square values of the demodulated acoustic emission signal using a data processor and storing the calculated root mean square values in the database;
  E) aligning in time the values of the root mean square of demodulated acoustic emission signal with values of the speed, the load and the temperature and storing the aligned values in the database; and
  F) using the aligned values of the root means square of demodulated acoustic emission signal, and the speed, the load and the temperature in a model which calculates at least one of the viscosity and the viscosity ratio from the aligned values, wherein the model is processed by the data processor and utilizes the speed, the load and the temperature.

11. A process according to claim 10, wherein the step of using the calculated value of the viscosity or the viscosity ratio in the bearing life model utilizes the calculated value of the viscosity.

12. A process according to claim 10, wherein the step of using the calculated value of the viscosity or the viscosity ratio in the bearing life model utilizes the calculated value of the viscosity ratio.

13. A process according to claim 10, wherein the root mean square values of the demodulated acoustic emission signal are calculated over an acquisition time of between zero point five (0.5) and thirty (30) seconds, and wherein the acquisition period is long enough to capture a minimum of four (4) rotations of the lubricated bearing.

* * * * *